United States Patent
Minor

(10) Patent No.: US 6,188,969 B1
(45) Date of Patent: Feb. 13, 2001

(54) MULTI-MEASUREMENT METHOD OF COMPARING AND NORMALIZING ASSAYS

(75) Inventor: James M. Minor, Los Altos, CA (US)

(73) Assignee: Chiron Corporation, Emeryville, CA (US)

(*) Notice: Under 35 U.S.C. 154(b), the term of this patent shall be extended for 0 days.

(21) Appl. No.: 09/031,124

(22) Filed: Feb. 26, 1998

(51) Int. Cl.[7] .................................................... G06F 19/00
(52) U.S. Cl. ................................ 702/86; 702/19; 702/22; 702/32
(58) Field of Search .................................. 702/86, 19, 22, 702/30, 32

(56) References Cited

PUBLICATIONS

M. Krajden, et al., "A Novel Method for comparison of Multiple Quantitative Assays: Evaluation of Three Commercial Assays for HBV DNA Quantification," Apr. 1997, poster presented at ASM Meeting.

M. Krajden, et al., "Multi–Measurement Method (MMM-)–Based Assessment of Commercial HBV DNA Assays and the Roche Amplicor HBV Monitor™ Test," Oct. 1997, Abstract of presentation at ASLD meeting.

M. Krajden et al., "Multi–Measurement Method (MMM-)–Based Assessment of FOur HBV DNA Assays," Nov. 1997, Abstract of presentation at Canadian Association for Clinical Microbiology and Infectious Disease Conference, St. Johns, Newfoundland.

Sophie Chiu, et al., "Use of Neural Networks to Analyze Drug Combination Interactions", pp. 56–61, 193, American Statistical Association 1993 Proceedings for the Biopharmaceutical Section.

James M. Minor, "Neural Networks for Drug Interaction Analysis," pp. 74–81, 1993, American Statistical Association 1993 Proceedings for the Biopharmaceutical Section.

Hamid Namini, et al., "Application of Neural Networks to Analyze Clinical Trial Data," pp. 82–87, 1993, American Statsticasl Association 1993 Proceedings for the Biopharmaceutical Section.

M. Krajden, et al., "Comparison of Performance Characteristics and Clinical Utility of Four HBV DNA Assays," poster presented at Second International Conference on Therapies for Viral Hepatitis, Kona, Hawaii, Dec. 1997.

Donald W. Marquardt, "An Algorithm for Least–Squares Estimation of Nonlinear Parameter," Jun. 2, 1963, pp. 431–441, *J. Soc. Indust. Appl. Math.*

Primary Examiner—Kamini Shah
Assistant Examiner—Hien Vo
(74) Attorney, Agent, or Firm—David P. Lentini; Jeffrey K. Weaver; Robert P. Blackburn

(57) ABSTRACT

A computer-implemented statistical technique is provided for normalizing the response curves of multiple measurement methods. The end result is a group of response curves, one for each measurement method under consideration, which depend on a common independent variable—the actual physical property being measured by the methods. The results are provided as a collection of equations, curves, and/or tables (a "nomogram") to facilitate conversion of measured values from one method to measured values from a second method. In the technique, data is provided for each of the methods being normalized. The input data includes measured values from common samples which are analyzed by two or more of the methods under consideration. The technique also requires assumptions or approximations of the true physical property values for each of the samples used to generate the data. Still further, the technique requires assumptions of the mathematical form of the response curves (e.g., linear, sigmoidal, etc.). The computer system then solves all parameters appearing in the mathematical expressions simultaneously. At the same time, the computer system solves for one or more "correction factors" to some of the approximations for the true physical property values of the samples. This specifies the relative separation distances between the physical property values on the independent variable axis.

25 Claims, 8 Drawing Sheets

|  | Linearity (curvature) | Responsiveness Sensitivity (slope) | Precision (scatter) |
|---|---|---|---|
| CA: | $Y = \underline{0.15}x^2 +$ | $\underline{3.79}x + 4.96;$ | $R^2 = \underline{0.9951}$ |
| DA: | $Y = 0.61x^2 +$ | $3.34x + 5.21;$ | $R^2 = 0.9946$ |
| RA: | $Y = 0.81x^2 +$ | $2.39x + 2.56;$ | $R^2 = 0.9614$ |
|  | Lower is better | Higher is better | Higher is better |

FIG. 6

MULTI-MEASUREMENT METHOD OF COMPARING AND NORMALIZING ASSAYS

BACKGROUND OF THE INVENTION

The present invention is directed to computer implemented statistical methods for comparing various assays or other measurement methods and converting between their results. More specifically, the present invention provides computer implemented statistical methods for determining the response curves of multiple measurement methods as defined for a single independent variable (which is the underlying property being quantitated by the methods).

Many assays and related tests quantify a physical property of a sample by comparing a measured assay value against an assay curve for the physical property of interest. For example, a blood sample may contain some initially unknown level of a particular pathogen. When the sample is evaluated with an assay for the pathogen of interest, it provides a measurable signal which tends to be proportional to the pathogen level in the patient's blood (at least in a log—log representation).

Examples of measured signals include luminescence or radiation emitted from a test sample, the absorption coefficient of the sample, the color of a sample, etc. In a typical case, the assay procedure involves contacting a test sample (analyte) with a test solution followed by a washing step. Thereafter, the test quantity of interest is measured and compared against an assay curve (sometimes referred to as a "response curve"). The assay curve provides the measured value as a dependent variable and the "true value" of the property of interest as an independent variable. In one specific example, an assayed sample of hepatitis B virus (HBV) DNA emits light of a luminescence that varies with viral load. Thus, the luminescence of the sample is detected and compared against the assay curve which specifies a corresponding value of viral load for the sample.

In most useful assays, the assay curve increases monotonically with the property of interest over the dynamic range (e.g., luminescence increases monotonically with viral load). Often the assay is designed so that the response of the assay is nearly linear over a specific dynamic range. To achieve this, the assay curve may be expressed as the logarithm of the measured value versus the logarithm of the property value. In practice, however, such assay curves rarely assume a truly linear form. Frequently, there is a slight curvature over the dynamic range which can be better represented by a quadratic expression. Further, near or just beyond the limits of the specific dynamic range, the response curve often flattens (i.e., the measured value changes only slightly with respect to changes in the true property value) to give the overall response curve a "sigmoid" shape.

Even with widely used and validated assays, one is never certain that the specified property value for a sample is truly accurate. For example, the calibration of an assay may be inaccurate because the "standard" used to generate the assay curve is itself inaccurate. Sometimes, the property value of a standard changes slightly with time. And sometimes when a standard runs out, the new standard created to replace the old does not possess the same true property value as the old standard. Further, while a given assay may be internally consistent over a period of time, it is still very difficult or impossible to accurately correlate two different assays for the same analyte.

Many applications could benefit from improved confidence in measurements of the property value consistent across assays. For example, one might want to use two or more different assays to monitor the same property value. A hepatitis B patient may have had his viral load monitored with a first assay that becomes temporarily unavailable. When a second assay—which relies on an entirely different physical mechanism than the first assay—is used in place of the first and gives a rather high reading of viral load, it could mean either (a) the patient's viral load is truly increasing or (b) the second assay employs an assay curve that, in comparison to the first assay's curve, gives a higher property value reading for a given sample. Obviously, an attending health care professional needs a reliable value consistent with both assays.

Also, parametric models for predicting the outcome of a medical treatment or other course of action are created from prognostic variables relevant to the models (e.g., assay results). The accuracy of the model is improved as more-consistent data is used to construct it. If that data is provided as assay results for two or more assays, there must be some way to establish a conversion between the assay results of the two or more assays. Otherwise the resulting model may fail to accurately handle inputs from one or more of the assays used to construct the model.

Other applications exist that require a conversion between property values specified by multiple assays or methods. For example, when an enterprise generates a new assay standard it must accurately correlate that standard's property value to the old standard's property value. Otherwise, assays using the new standard will not be consistent with the same assays using the old standard.

In another example, enterprises may need to compare two assays' performance (e.g., sensitivity and responsiveness) when those assays are designed to quantitate the same analyte. Several commercial assays are available for HBV DNA quantification, and laboratory managers need tools to assess how well the various assays operate. Even when results are reported in the same unit of quantification for a given sample, different assays report different results. Thus, the person conducting the comparison must ensure that the response curves of the two assays can be plotted on the same independent variable axis (the true property value axis).

Traditionally, when comparing multiple assays or batches of a standard, one uses a regression analysis to quantify the associations of interest. For example, for a series of samples, the measured values of a first assay or batch is provided as the independent variable and the measured values of the second assay or batch is provided as the dependent variable. Then one assumes a relationship between the independent and dependent variables (e.g., a linear or quadratic relationship) and a regression analysis is performed to identify parameters of the relationship that nicely fit the data. Unfortunately, linear regression analysis is restricted to comparison of only two assays at a time. Still further, this application of regression tends to violate a primary assumption for correct inference of results, i.e., the independent variable is assumed to be more precise versus the dependent variable. See e.g., Yonathan Bard, "Nonlinear Parametric Estimation," Academic Press, New York, N.Y., 1974. Hence, the more precise variable must be the independent regression variable, typically denoted as x, while the noisier variable must be the dependent or response variable, denoted y. In many assay comparisons, where one assay is selected to be y variable and the other x variable, the results are questionable since the assay errors are comparable or, worse, the x variable error is larger than the y variable error.

Hence, there is a need to compare multiple assays (or other methods) or batches of standard without the inherent bias of linear regression, to be able to convert values between the different assays or standards, and to provide a property basis consistent across all assays.

SUMMARY OF THE INVENTION

The present invention provides computer implemented statistical techniques for normalizing the response curves of multiple measurement methods. This permits, inter alia, evaluation of multiple methods, conversion of their results, and normalization of assay standards. These techniques allow comparative assessment of two or more measurement methods at one time and significantly reduce the bias as compared to the typical regression methods. The end result is a group of response curves, one for each measurement method under consideration, which depend on a common independent variable—the actual physical property being measured by the methods. The response curves may be provided as a collection of equations for the curves, plots of the curves, and/or tables (collectively a "nomogram") to facilitate conversion of measured values from one method to expected measured values of any other method.

In the technique, the computer receives data for each of the methods being normalized. The data includes measured values from common samples which are analyzed by two or more of the methods under consideration. The technique also requires assignments or approximations of the true physical property values for each of the samples used to generate the data (e.g., sample 1 has concentration of 1M, sample 2 has a concentration of 2M, etc.). Still further, the technique requires assumptions of consistency within each assay expressed in mathematical form as the response curves (e.g., the response of assay 1 is linear, the response of assay 2 is sigmoidal, etc.). The computer system then solves all parameters appearing in the mathematical expressions simultaneously (e.g., it solves for the slope and intercept of a linear response curve). Simultaneously, the computer system solves for one or more "correction factors" to some of the approximations for the true physical property values of the samples. When solved, these correction factors correct the relative separation distances between the initial approximations of physical property values on the independent variable axis, thereby reducing errors in x-axis values and improving self-consistency across assays. In the end, each response curve is provided on a common x-axis, thereby allowing direct comparison and conversion.

In one aspect, the computer implemented methods of this invention may be characterized by the following sequence: (a) receiving data specifying measured values versus physical properties or samples evaluated by the two or more measurement methods; (b) assuming a value for the physical property of a first sample (tested by at least two of the methods) and assuming a value for the physical property of a second sample (also tested by at least two of the methods); (c) for each of the two or more measurement methods, assuming a mathematical form of a response curve; and (d) simultaneously solving for all unknown parameter values of the response curves and for a correction factor for the value of the physical property of the second sample. The input data should include at least enough data points to fully determine the parameter values of the response curve, the correction factor for the second sample, and any additional correction factors for other physical property values (associated with additional samples that were analyzed by two or more of the methods).

The mathematical form of the response curve may be any monotonic non-constant function. Examples include linear expressions, quadratic expressions, and sigmoidal expressions. Examples of unknown parameters values solved for with this invention include the slope and intercept of a line, the curvature of a quadratic expression, etc. The computer implemented method may output a nomogram including solved response curves or solved mathematical expressions for at least two of the measurement methods.

The method is invariant (indeterminant) with respect to translations on the x-axis. Therefore a constraint is added to enable a solution to the equations. One such constraint (but not the only possible constraint) is an "anchoring procedure." Typically, when the method simultaneously solves for the parameter values, it will solve for multiple correction factors, each associated with the physical quantity of a sample for which data was received. Prior to solving the expressions, however, one of the physical property values is set as an "anchor value." During simultaneously solving for all the unknown parameter values, the anchor value is not provided with a correction value.

These and other features and advantages of the present invention will be presented in more detail in the following description of the invention and the associated drawings.

BRIEF DESCRIPTION OF THE DRAWINGS

FIG. 6 presents the mathematical expressions for the three response curves shown in FIG. 5.

DETAILED DESCRIPTION OF THE PREFERRED EMBODIMENTS

A. OVERVIEW

Figure 1:
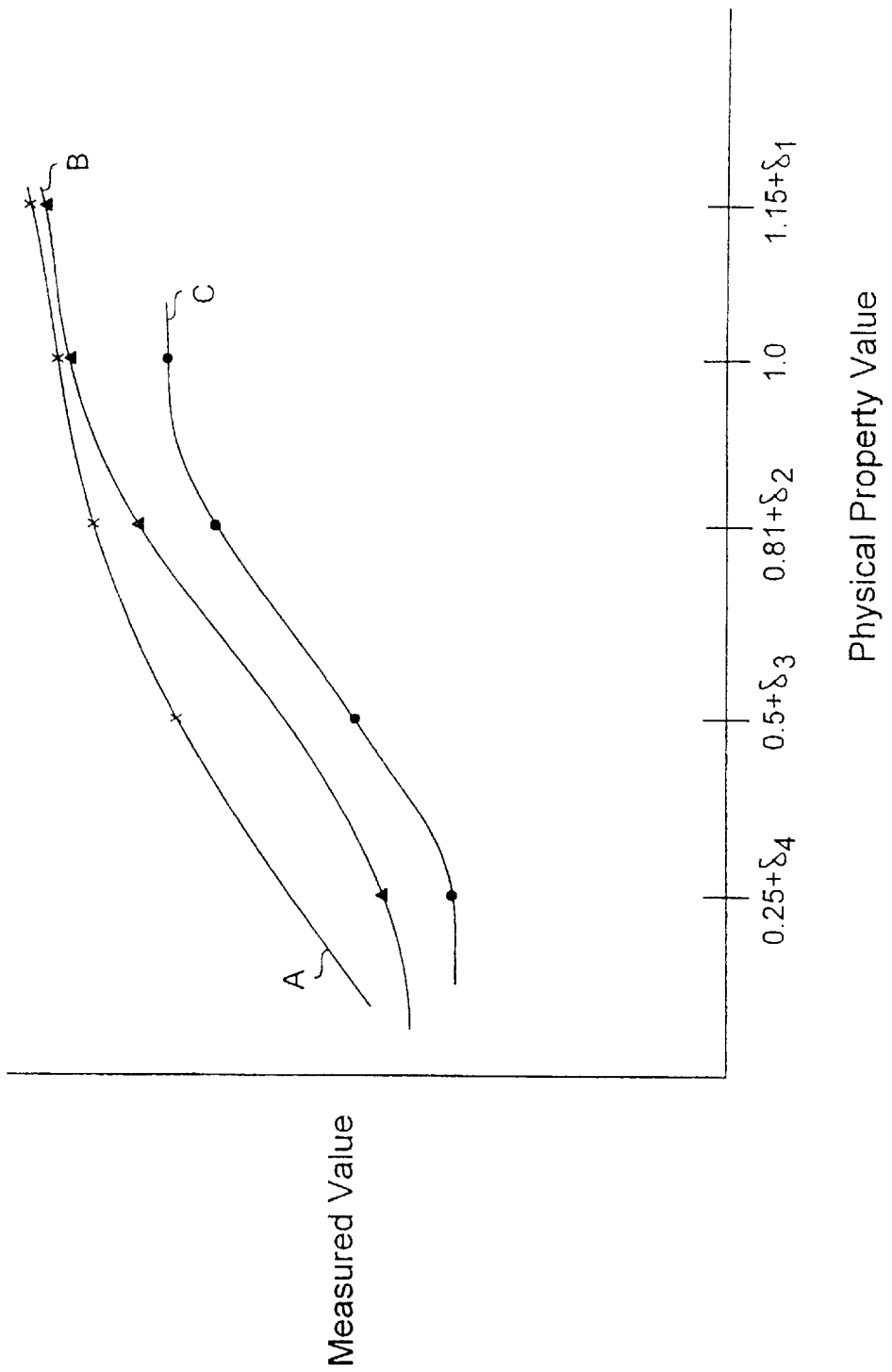
FIG. 1 is a graph of hypothetical data indicating the response of three separate measurement methods and application of one method of this invention.

The present invention provides techniques and systems for normalizing measurement results such that data taken by multiple measurement methods is provided on a common independent variable axis. This multi-measurement technique is a minimal bias, non-linear regression technique that can evaluate the performance characteristics of multiple methods and produce a conversion between the readings of the multiple methods. The invention accomplishes this by simultaneously solving for parameters in expressions for response curves and correction factors applied to the data values of the independent variables.

In the following description, various specific details are set forth in order to fully illustrate preferred embodiments for accomplishing the analysis of this invention. For example, certain specific applications of the invention (e.g., comparing multiple assays for HBV DNA) will be described. It will be apparent, however, that the invention may be practiced without limitation to the specified details and applications presented herein. Based on principles similar to those that govern least squares analysis, neural networks, latent analysis, and principle component analysis, the multi-measurement technique of this invention assumes that all measurement techniques being compared are measuring the same unknown physical property (e.g., analyte concentration in the case of assays). The multi-measurement technique fits the multiple data sets from different assays to determine the optimal interrelationships between the data sets such that a consistent "true" physical property is derived. These "true" values represent an intrinsic component of what is being measured by each assay (e.g., HBV DNA concentration), and serves as the unifying factor for all assays being compared. The measured assay values (typically provided as natural logarithms) for each specimen are designated as dependent (y) variables while approximate "true" values are designated as independent (x) variables. Approximation of the "true" physical property (x) in each specimen may be performed in a two-stage process. First, an initial approximation of analyte concentration (e.g., viral load), designated x', is obtained by normalizing the input values (usually via natural logarithm values) for each specimen tested by assays being compared, and averaging the log values for each specimen. The method may, during the averaging, weight each measurement by the sensitivity of the corresponding assay; i.e., results from steeper slope assays get higher weights.

Then, the calibration function (expression for the response curve) and corrections to analyte concentration approximations, designated δ, are estimated simultaneously for all specimens by non-linear regression. The approximated "true" analyte concentration (x value) in each specimen is calculated using the equation: x=x'+δ. Once x' is corrected to x, it is used to generate a multi-measurement technique nomogram.

The response curves on this nomogram may be plotted on a log transformed scale, where the y-axis indicates the measurement levels for the specimens measured by each of the assays (in the various log assay units), and the x-axis indicates the corrected "true" analyte log concentration in each specimen as generated by the multi-measurement technique. Features of the assay curves, including curvature, slope, and the degree of scatter about the curve, differ for each assay and provide comparative information about each assay's performance characteristics and allow direct comparisons at each location on the x-axis.

The multi-measurement technique of this invention enhances the value of measurement method quantification in several ways. First, the multi-measurement technique allows performance characteristic comparison and interassay value conversion among multiple assays simultaneously. Second, it assesses and optimizes analytical standards to facilitate development of more precise and reliable assays. Third, normalization of assay values allows researchers, scientists, physicians, or other professional using measurement techniques to make sense of results reported from different assays with different units and standardization. This is because the response curves and equations generated by the multi-measurement technique make it possible to convert among measurements of each method.

As mentioned, conventional assay evaluations using linear regression analysis promote internal bias because the assay depicted on the x-axis (the independent variable) is assumed to be significantly more precise than the assay depicted on the y-axis (the dependent variable). Unlike linear regression, the multi-measurement technique simultaneously estimates the true value of the analyte and the curves that associate each assay's results with this value by assuming that all measured values (e.g., luminescence) for each measurement method are dependent variables A new more precise independent variable is constructed that represents an intrinsic quality of what is being measured by all the assays, such as the viral load and relates each assay to the others.

To briefly illustrate techniques of this invention, FIG. 1 presents a graph of hypothetical data indicating the response of three separate measurement methods. The y-axis (vertical axis) represents the value of the measured quantities for each of the measurement methods. Because these methods may employ different measurement quantities (e.g., luminescence in one case and absorptivity in another case and radioactivity in yet another case), the y-axis normally encompasses multiple units which have an arbitrary relation to one another. Typically the relation is chosen so that all response curves can be viewed together (e.g., log measurement). The x-axis (the horizontal axis) represents the value of the underlying physical property which is being measured. This axis will, of course, present only a single type of units (e.g., concentration of viral DNA) and will be consistent from method to method. For many applications, the absolute magnitudes of the units on the x-axis need not be known because the techniques of this invention are merely making the multiple measurement methods internally consistent with respect to the underlying physical property. Thus, in many embodiments, an "anchor" value is arbitrarily chosen on the x-axis and all other values on the x-axis are chosen and corrected relative to the anchor.

In the hypothetical example of FIG. 1, three independent clinical samples are provided for analysis. They may be blood samples of patients infected with HBV for example. These samples have unknown values of the underlying physical properties which can be approximated by a variety of techniques. In this case, the initial approximations were 0.81 for a first sample, 1.0 for a second sample, and 1.15 for a third sample. In addition, two dilutions of the first sample are made. In the first dilution, the sample was diluted by 50% to approximately 0.5. In the second dilution, the first dilution was further diluted by 50% to approximately 0.25. These approximate sample (and dilution) values are presented on the x-axis.

Each of the samples was tested by two or more of the three measurement methods. The data points for a measurement method denoted "A" are shown as "X"s, the data points for a second measurement method denoted "B" are shown as triangles, and the data points for a third measurement method denoted "C" are shown as round dots. The first sample was tested by all three methods as indicated by data points for x=0.81 on response curves of all three measurement methods. The second sample was also tested by all three methods (data points for x=1.0). The first dilution of the second sample was tested by the first and third (A and C) measurement methods, and the second dilution of the second sample was tested by the second and third (B and C) measurement methods. Finally, the third sample (x=1.15) was tested by the first and second methods (A and B).

The data points shown in FIG. 1 may represent the processed result of multiple data points taken with a given method using a specified sample. To improve the accuracy of the inventive technique, multiple measurements ("replicates") may be taken for some or all of the method/ sample combinations. All measurements show some randomness or scatter when taken multiple times. Typically the scatter may be reflected as a Gaussian or normal distribution having a mean and standard deviation. In a preferred embodiment, all individual data points are input —without assuming the form of a noise distibution (Gaussian, log normal, etc.). The method then determines the best fit curve passing a minimized distance from each mean.

In this example, the second sample was chosen as the anchor value and given a value of 1.0 on the x-axis. Its first and second dilutions were therefore given values of 0.5 and 0.25 respectively. As mentioned, the x values of the first and third samples were approximated to be 0.81 and 1.15, respectively. Except for the anchor value, all sample and dilution values were provided with a correction factor, $\delta$. The values of these correction factors are solved by the computer techniques of this invention to improve the accuracy of the relative positions of the samples on the x-axis. Simultaneously with the solution of the x-axis correction factors, the technique solves the various parameters used in the expressions for the response curves. If a curve is assumed to be quadratic, for example, the technique must solve for the intercept, b, the linear component of slope, m, and the curvature, k. The relevant expression is $y=kx^2+mx+b$.

In one particular example, the response curves of all three measurement techniques are assumed to be quadratic in order to account for some curvature over their dynamic ranges. The computer system receives the data points shown in FIG. 1 (which may actually represent the processed readings of multiple readings taken for each sample/method combination). It assumes the quadratic forms of the response curves and the initial approximations of the underlying property values (x-axis positions) of the samples. This means that there are several unknowns to be solved. These are (1) a correction factor, $\delta$, for each x value of the sample except the anchor value and (2) an intercept, b, a slope, m, and a curvature coefficient, k, for each response curve.

Specifically, the parameters to be solved are $k_A$, $m_A$, $b_A$, $k_B$, $m_B$, $b_B$, $k_C$, $m_C$, $b_C$, $\delta_1$, $\delta_2$, $\delta_3$, and $\delta_4$. These parameters may be solved simultaneously by a computer system implementing a non-regression technique, for example.

Preferred embodiments of this invention make certain assumptions about the methods being analyzed and the data input to the techniques of this invention. That is, certain criteria must be met in order for the normalizing procedures of this invention to work. These assumptions are the following.

First, multiple measurement methods for assessing the same physical property must be compared together. The techniques of this invention do not act on just one method. Obviously, two mechanistically different assays for quantifying HBV DNA meet this criterion. However, the range of methods that qualify is broader than this. For example, because a given assay may behave slightly differently when conducted under slightly different conditions, a single assay when conducted under these slightly different conditions may form the basis of two or more independent methods which can be employed with the multi-measurement technique of this invention. For example, one company's HBV DNA assay may be performed with two different standards or on two different assay plates to provide two distinct methods as required to meet this criterion.

Second, samples to be corrected in the multiple measurement technique must be measured by at least two of the measurement methods under consideration. Thus, a first sample will be measured with two or more of the methods, a different sample will be measured with two or more of the methods (not necessarily the same methods used with the first sample), etc. Of course, each different sample must contain the same analyte of interest—albeit at different levels—so that all methods measure the equivalent property.

Third, for each method, the number and distribution of data points (measured values for samples under consideration) is adequate to fully determine each of the parameters required to specify the assumed form of the response curves (e.g., two unique x points for a line (slope and intercept), three unique x points for a quadratic curve, etc.). The minimum total of all properly distributed data required to handle all measurement methods in the normalization is the sum of the number of parameters for each method curve plus the number of samples to be corrected used to generate the data plus one (for an anchor x value). This additional requirement is imposed by correction factors for all samples except one (designated as the anchor value). As explained, these correction factors are provided to allow adjustment of the relative position of the sample values but they are additional parameters that must be solved for.

Fourth, each individual measurement method has the property of reasonable continuity or smoothness as the hidden phenomena varies. In addition, the response curves must be monotonic and non-constant. Thus, it can not have two values of the underlying property for any one measured value (i.e., a one-to-one mapping between measured value and underlying property is required).

B. COMPUTER SYSTEMS FOR IMPLEMENTING THE INVENTION

Embodiments of the present invention as described herein employ various process steps involving data stored in or transferred through computer systems. The manipulations performed in implementing this invention are often referred to in terms such as calculating, normalizing, or solving. Any such terms describing the operation of this invention are machine operations. Useful machines for performing the operations of embodiments of the present invention include general or special purpose digital computers or other similar devices. In all cases, there is a distinction between the method of operations in operating a computer and the method of computation itself. Embodiments of the present invention relate to method steps for operating a computer in processing electrical or other physical signals to generate other desired physical signals.

Embodiments of the present invention also relate to an apparatus for performing these operations. This apparatus may be specially constructed for the required purposes, or it may be a general purpose computer selectively activated or reconfigured by a computer program and/or data structure stored in the computer. The processes presented herein are not inherently related to any particular computer or other apparatus. In particular, various general purpose machines may be used with programs written in accordance with the teachings herein, or it may be more convenient to construct a more specialized apparatus to perform the required method steps. The required structure for a variety of these machines will appear from the description given below.

In addition, embodiments of the present invention further relate to computer readable media or computer program products that include program instructions and/or data (including data structures) for performing various computer-implemented operations. The media and program instructions may be those specially designed and constructed for the purposes of the present invention, or they may be of the kind well known and available to those having skill in the computer software arts. Examples of computer-readable media include, but are not limited to, magnetic media such as hard disks, floppy disks, and magnetic tape; optical media such as CD-ROM disks; magneto-optical media such as floptical disks; and hardware devices that are specially configured to store and perform program instructions, such as read-only memory devices (ROM) and random access memory (RAM). Examples of program instructions include both machine code, such as produced by a compiler, and files containing higher level code that may be executed by the computer using an interpreter.

Figure 2:
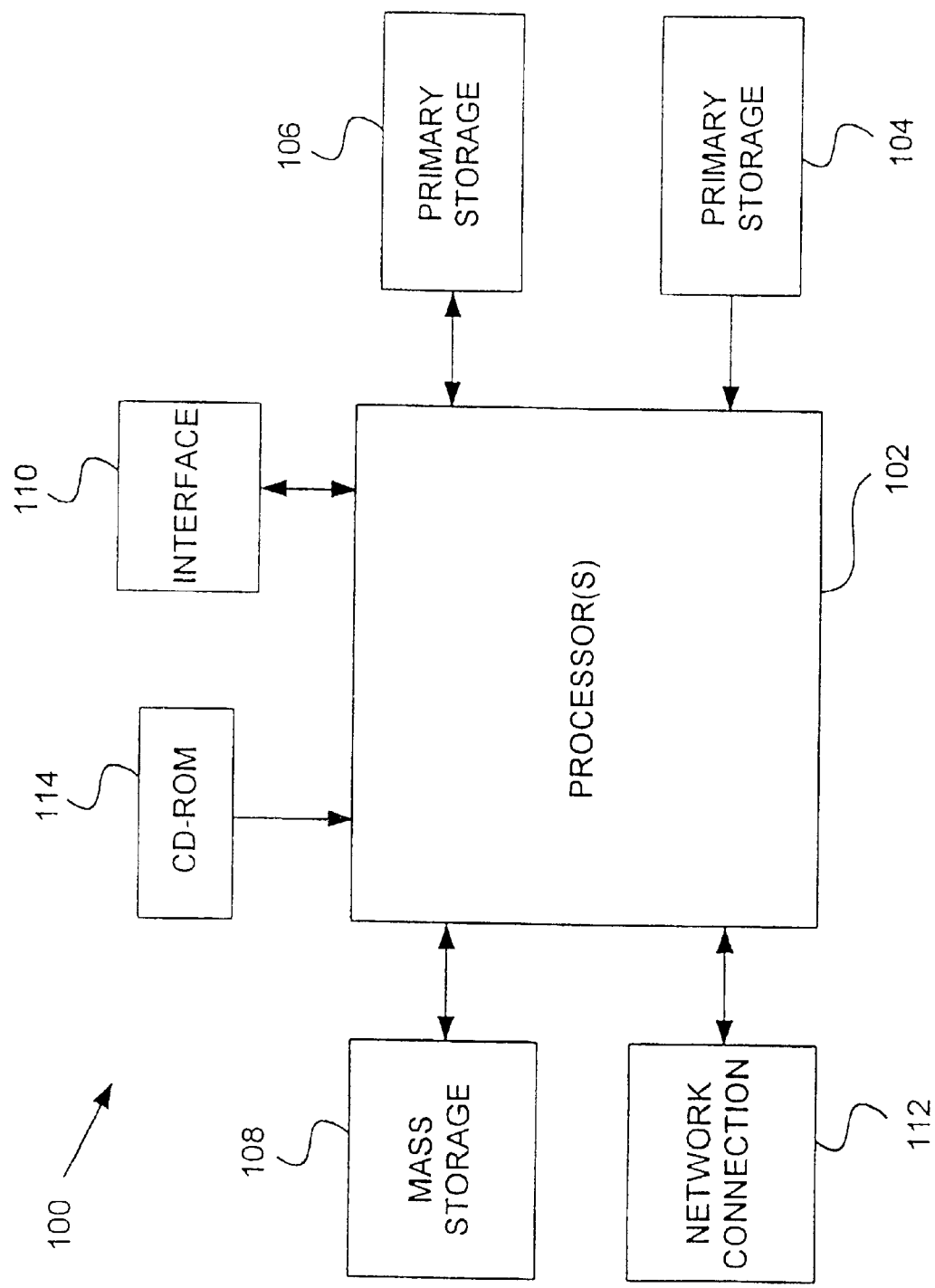
FIG. 2 is a block diagram of a generic computer system useful for implementing the present invention.

FIG. 2 illustrates a typical computer system in accordance with an embodiment of the present invention. The computer system 100 includes any number of processors 102 (also referred to as central processing units, or CPUs) that are coupled to storage devices including primary storage 106 (typically a random access memory, or RAM), primary storage 104 (typically a read only memory, or ROM). As is well known in the art, primary storage 104 acts to transfer data and instructions uni-directionally to the CPU and primary storage 106 is used typically to transfer data and instructions in a bi-directional manner Both of these primary storage devices may include any suitable computer-readable media such as those described above. A mass storage device 108 is also coupled bi-directionally to CPU 102 and provides additional data storage capacity and may include any of the computer-readable media described above. Mass storage device 108 may be used to store programs, data and the like and is typically a secondary storage medium such as a hard disk that is slower than primary storage. It will be appreciated that the information retained within the mass storage device 108, may, in appropriate cases, be incorporated in standard fashion as part of primary storage 106 as virtual memory. A specific mass storage device such as a CD-ROM 114 may also pass data uni-directionally to the CPU.

CPU 102 is also coupled to an interface 110 that includes one or more input/output devices such as such as video monitors, track balls, mice, keyboards, microphones, touch-sensitive displays, transducer card readers, magnetic or paper tape readers, tablets, styluses, voice or handwriting recognizers, or other well-known input devices such as, of course, other computers. Finally, CPU 102 optionally may be coupled to a computer or telecommunications network using a network connection as shown generally at 112. With such a network connection, it is contemplated that the CPU might receive information from the network, or might output information to the network in the course of performing the above-described method steps. The above-described devices and materials will be familiar to those of skill in the computer hardware and software arts.

The hardware elements described above may implement the instructions of multiple software modules for performing the operations of this invention. For example, instructions for matching selection vectors to patient electronic profiles (in electronic discharge records for example) may be stored on mass storage device 108 or 114 and executed on CPU 108 in conjunction with primary memory 106.

C. PROCEDURES

Figure 3:
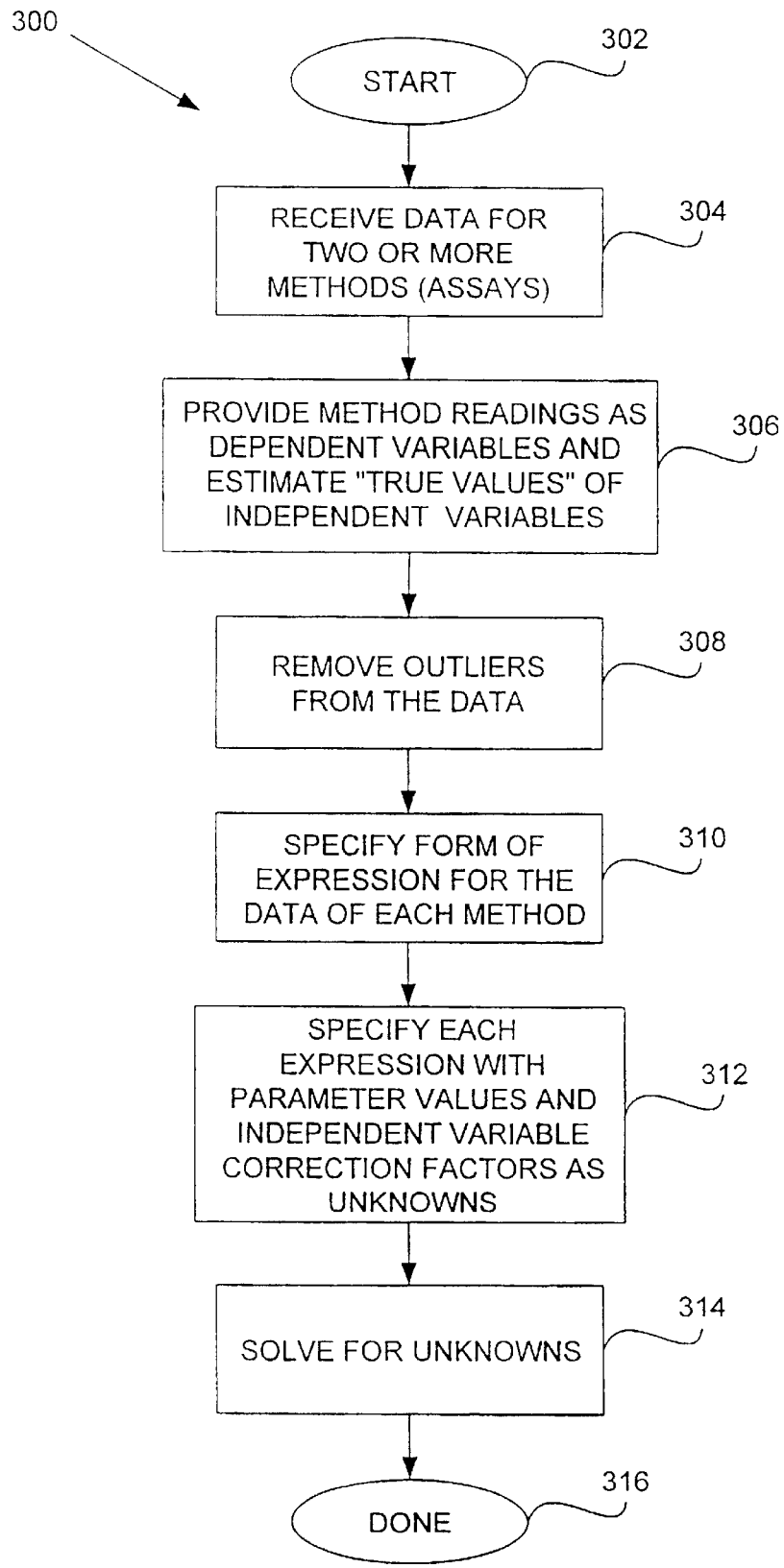
FIG. 3 is a process flow diagram depicting some of the important steps employed in a preferred computer implement technique of this invention.

FIG. 3 is a process flow diagram illustrating some of the important steps that may be employed in a preferred embodiment of the present invention. At least some of these steps are implemented as software or machine operations on an appropriately configured computer system as described above. These operations are preferably performed sequentially, in a continuous fashion, by the software and/or appropriately configured machine. It is, of course, possible that various steps described here are performed by two or more separately operating pieces of software or appropriately configured machines.

As shown in FIG. 3, a process 300 begins at 302 and then in a step 304, the system receives data for two or more methods. As explained above and in more detail below, these methods will typically be assays or other appropriate test procedure for which results (data) are generated.

After the appropriate data for the two or more methods has been input at step 304, the system next arranges the data so that the results (e.g., assay readings) are the dependent variables and the "true values" of the physical property or other data reflected by the observed results are the independent variables. Sometimes it will be necessary to estimate the "true values" of the independent variables. Often, a first estimate of such independent variables is simply the value attributed to the independent variable by the current calibration curve for the assay at issue. In FIG. 3, this step of arranging the dependent and independent variables is performed by the system at a step 306.

Next, at an optional step 308, the system "cleans up" the data by removing outliers and/or "noise" data which is clearly erroneous. Hence, the effects of outliers and erroneous results tend to be filtered out. This reduces the impact of atypical data on the performance of the technique. Outliers are the data points that most clearly fall outside of the expected range of measured values. Usually, they are the result of experimental error or other problem unrelated to the sample. Thus, step 308 serves to improve the quality of the nomograms generated by the methods of this invention.

As shown in FIG. 3, at a step 310, the forms of the response curve expressions must be specified for each method. For example, the response curve may be specified as linear, quadratic, sigmoidal, etc. The form of an expression for an assay is often provided by the vendor of that assay in the form of a calibration curve, for example. Sometimes, in order to simplify the functional form of the curve and to simplify the noise distribution over a dynamic range, logarithms of the dependent and independent variables are used.

Once the form of the expression or expressions have been set, the mathematical relationships between various parameters are given. These parameters and their corresponding relationships (as specified by the mathematical expression) are now in a form that can be solved, given a sufficiently complete set of data. As indicated at step 312, the system receives or specifies these expressions with the appropriate parameter values. In addition, the expressions include one or more correction factors which are provided as unknowns. Thereafter, the unknowns (the parameters for the expressions and the correction factors for the independent variables) are solved as a system of equations at a step 314. These values are output and the process is completed at 316.

While process 300 is presented as a defined sequence of process steps. The invention is not limited to software and system that performs each and every one of these steps. For example, it is not necessarily limited to systems that remove "outliers" or automatically postulate the form of the expressions of the methods. Nor is the invention limited to processes which perform steps in the exact order specified by the flow chart of FIG. 3.

The data used in the methods of this invention is obtained from multiple samples which are used in the various assays to generate measured values. Generally, these samples are independently provided (e.g., from various clinical samples and/or from specially made standards) so that their relative positions with respect to one another on the independent variable axis are not accurately known. In some cases, some or all of the samples form a dilution series. That is, one sample, the original and most concentrated sample, serves as the concentrate. Other samples are created by diluting the concentrate with fixed amounts of the diluent. The relative positions of the dilution series members are rather clear, but the positioning accuracy is limited by the dilution accuracy. So some small correction between the relative positions of the dilution series samples may still be required, a single larger percentage correction can be applied to the original and appropriately proportioned to each dilution member. In log space, this simply shifts the dilution sequence as an ensemble by the correction amount. To improve the quality of the input data, some samples may be measured multiple times with the same assay. These multiple readings will produce a spread in the measured values.

The techniques of this invention require enough good data points (combinations of methods and samples) to completely "determine" the system. That is, the number of data points should at least equal the number of parameters and correction factors specified in 312 plus one.

As indicated at step 306, the method readings (results or observations) are provided as the dependent variables and the "true values" of the variable being measured are provided as the independent variables. For example, in an assay for a particular biological compound or organism, the dependent variables may be readings of luminances, radioactivity, color, etc. Typically, the vendor will provide a calibration curve which correlates these observed outputs with the independent variables. As mentioned above, one is never completely sure that the "true values" of the independent variables are in fact accurate. Correcting the relation of these "true values" with multiple assays is a primary goal of this invention.

Figure 4:
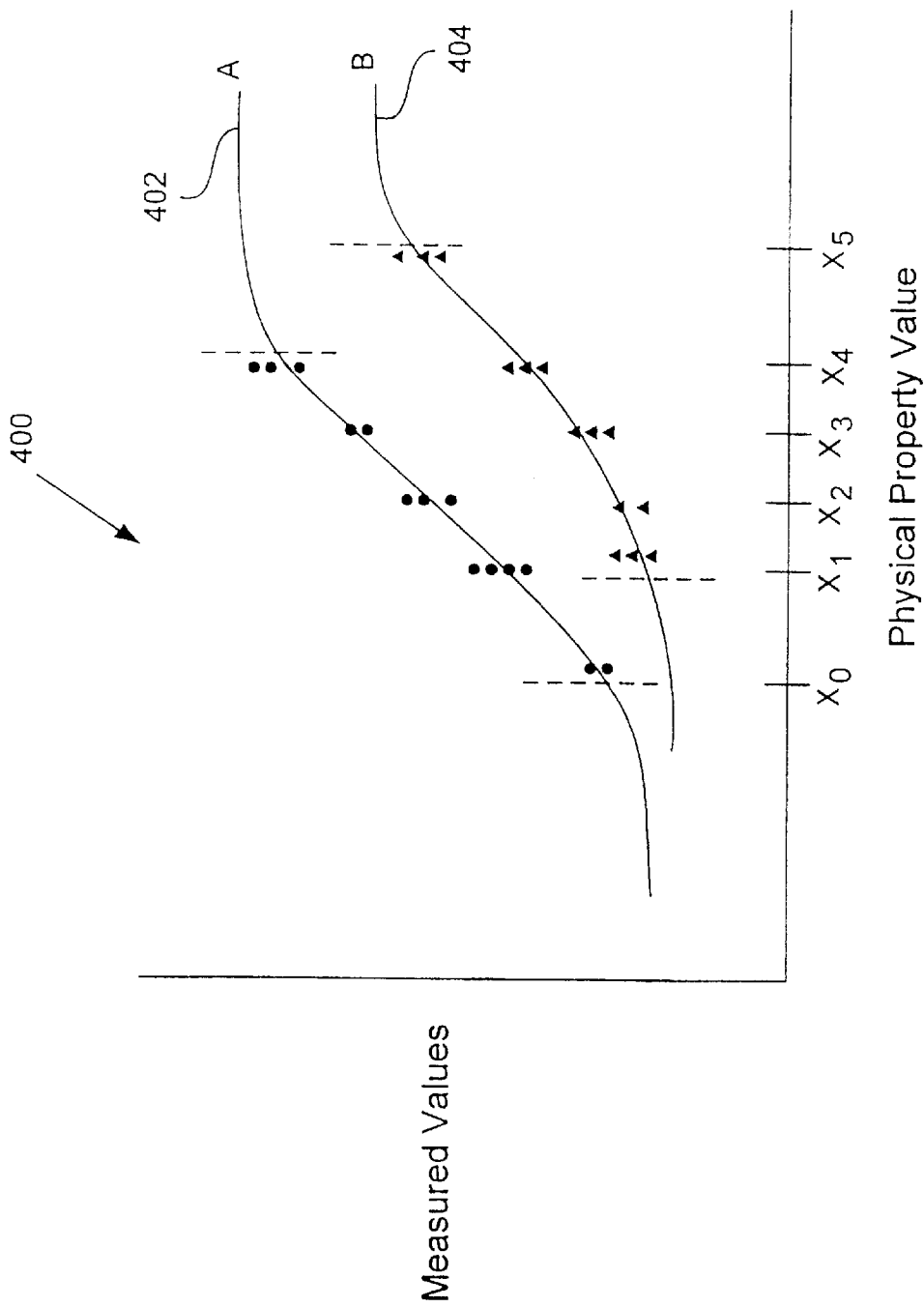
FIG. 4 is a graph of hypothetical data illustrating some of the steps presented in FIG. 3.

Referring now to FIG. 4, a hypothetical plot 400 presents an observed result on the y-axis as a function of the true value on the x-axis for two hypothetical assays. A first response curve 402 represents the expected behavior of a first assay (assay A) and a second response curve 404 represents the expected behavior of a second assay (assay B). Note that both curves 402 and 404 are fairly linear over a dynamic range (bounded by dashed vertical lines) but decrease in slope near the maximum and minimum regions of the dynamic range. Thus, the overall shape of curves 402 and 404 may be characterized as sigmoidal. This response is typical of many conventional assays.

Generally, the data will clearly show a trend indicative of the form of a mathematical expression (e.g., linear). When the data is taken from a well characterized assay or other test, an appropriate form of the mathematical expression may be provided in the literature. Curves 402 and 404 are generally linear in a central region represented by their dynamic ranges, although curve 404 is sufficiently curved that it will be fit with a quadratic expression in this illustration.

Initial locations of the samples on the x-axis must be approximated. Some specially made samples will have "bottle values" (i.e., assigned approximate concentrations). However, other samples such as clinical samples may have no preassumed property value. For these, fairly reasonable initial property values must be provided. The normalization technique of this invention will then correct the values through the correction factors on the x values. One suitable technique for approximating the x value of unknown samples is to take the average of the measured results (y values) for the assays used to measure it weighted by sensitivity (steepness of slope). At first blush, this may seem odd because the average gives a y value, not an x value. However, because the response curves are assumed to be monotonic, the order and relative positions of the approximated x values for the samples will be roughly correct and random error is reduced by the averaging process. The x-axis will tend to represent assay readings and the measured property indirectly. One can average the logarithm of the quantitated property value across assays weighted by the sensitivity of each assay. Sensitivity is the steepness of the slope of logarithm assay readings versus quantitated properties.

Before solving the set of expressions simultaneously, the anchor value must be chosen. This is the x value of one of the samples. Typically, the anchor value is chosen for the sample whose property value is most trusted. All x values of the other samples are defined relative to the anchor value. Therefore, all other sample x values on the axis are calculated based upon their relations to the anchor value. To attain this, correction factors are added to all property values on the independent variable axis (the values for which samples were produced) except the one referenced as the anchor value.

Various mathematical expressions for the response curves may be employed. While any monotonic non-constant function will work as an expression for the response curves, simpler expressions are preferred as they require fewer parameters. Each additional parameter removes a degree of freedom from the system. That is, additional data points are required to completely determine the system. Preferred expressions for response curves include linear expressions, quadratic expressions, and sigmoidal expressions.

If a data curve is postulated to be a line (step 310), then the form of the equation is $$y=mx+b$$

with m representing the slope of the line and b representing the line's intercept. These parameters must ultimately be solved for in step 314.

If the data curve is postulated to be a quadratic curve, the form of the equation is $$y=kx^2+mx+b$$

where the parameters are as defined above, and "k" is the quadratic term coefficient. In this case, k, m, and b must be for in step 314.

If the data curve is postulated to be a symmetrical sigmoid, then it may be represented by the expression $$y=a+b/(1+\exp(-cx+d))$$

In this expression, the slope of the sigmoid is bc/4 at x=d/c, and a, b, c, and d must be solved for in step 314. Asymmetrical sigmoids may be better than symmetrical sigmoids at fitting some data. Any modification of the above expression which removes the symmetry of the derivative of y with respect to x will introduce an asymmetry in the sigmoid; however the derivative must be greater than zero for all x. Specific examples of asymmetric sigmoids include those in which the function "−cx+d" in the above expression is replaced with (−clnx+d), (−cx$^2$+d) (for any non-negative x), or any nonlinear polynomial constrained to satisfy the above derivative requirements. Applications of asymmetric sigmoid functions are described in Chiu et al., "Use of Neural Networks to Analyze Drug Combination Interactions," American Statistical Assoc. 1993 Proceedings of the Biopharmaceutical Section, pp 56–59 and J. Minor, "Neural Networks for Drug Interaction Analysis," American Statistical Assoc. 1993 Proceedings of the Biopharmaceutical Section, pp. 74–81. Both of these references are incorporated herein by reference in their entireties and for all purposes.

Before the parameter values can be solved, the expression for each method is written with a correction factor for the value of the independent variable x (step 312). The quadratic form, for example, is then written as $$y = k(x1+\delta 1)^2 + m(x1+\delta 1) + b$$

where $\delta 1$ is the correction factor for the particular sample corresponding to the current value of x(x1). For each sample used for a particular method, the appropriate mathematical expression is provided with the independent variable expressed as x+δ. Together these expressions are solved to yield the parameter values and the correction factors for the independent variables.

Given the data set presented in graph 400, the relevant expressions for simultaneous solution are now presented. Note again that response curve 402 (method A) is assumed to be linear over its dynamic range and the response curve 404 (method B) is assumed to be quadratic over its dynamic range. Typically, these values are input as matrix coefficients or are organized as such by the computer system.

$$yA0 = m_A(x0+\delta 0) + b_A$$

$$yA1 = m_A(x1) + b_A$$

$$yA2 = m_A(x2+\delta 2) + b_A$$

$$yA3 = m_A(x3+\delta 3) + b_A$$

$$yA4 = m_A(x4+\delta 4) + b_A$$

$$yB1 = k(x1)^2 + m_B(x1) + b_B$$

$$yB2 = k(x2+\delta 2)^2 + m_B(x2+\delta 2) + b_B$$

$$yB3 = k(x3+\delta 3)^2 + m_B(x3+\delta 3) + b_B$$

$$yB4 = k(x4+\delta 4)^2 + m_B(x4+\delta 4) + b_B$$

$$yB5 = k(x5+\delta 5)^2 + m_B(x5+\delta 5) + b_B$$

Note that these expressions do not account for replicate measurements for given assay/sample combinations. For example, there are two replicates at x0 for assay A. In preferred embodiments, the systems of this invention generate a separate expression for each replicate.

Thus, there will actually be two expressions for sample x0 as evaluated by assay A. These expressions will be identical, save the y value. In this example, rather than using the single expression $yA0 = m_A(x0+\delta 0) + b_A$ for sample x0/assay A, the system would actually generate two expressions:

$$yA0_1 = m_A(x0+\delta 0) + b_A \text{ and}$$

$$yA0_2 = m_A(x0+\delta 0) + b_A$$

All expressions for all data points are then solved together (step 314) to yield the parameters $m_A$, $b_A$ (the slope and intercept of curve 402), k, $m_B$, and $b_B$ (the curvature, slope and intercept of curve 404) and correction values ($\delta 0$, $\delta 2$, $\delta 3$, $\delta 4$, and $\delta 5$). Note that x1 is the anchor value. Note also that this system is completely determined but not over determined; there are 10 unknowns and 10 equations (one for each data point). Often the system must be over determined; that is, there will be more expressions (data points) than unknowns in order to estimate precision (assay noise).

The unknown parameters may be solved by a non-linear regression technique. Such techniques take as their objection functions the sum of the squares of the residuals (summed over all data points). Other solution techniques such as maximum entropy, minimum entropy, and maximum likelihood have other objective functions. In each case, the technique solves the unknowns by minimizing the objective function which is a function of the unknown parameters that measures optimal fit to the data. A computer technique performs the required minimization over multiple iterations until the problem converges.

The residual used in the sum of squares of residuals objective function is given by $$R = Y_j - f(X_j, \delta_i, \beta_i)$$

where j identifies the data point under consideration, i identifies the current iteration in an iterative technique to minimize the cost function, Y is the actual measured value of data point j, f is the functional form of the response curve (e.g., quadratic), δ is the correction factor for the sample used in data point j, β is the structural parameter (or parameters) used in the functional form (e.g., k, m, and b for a quadratic), and R is the residual. The sum of squares of residuals cost function is simply $\Sigma(R_j)^2$ over all values of j (i.e., over all data points). Note that in conventional regression techniques, the values of $X_j$ are assumed to be precise. In contrast, the methods and systems of this invention initially take the $X_j$ as imprecise and then correct them to be precise.

The present invention preferably, though not necessarily, employs a Marquardt-Levenberg method, which is an iterative method to minimize the cost function, whatever it may be. D. W. Marquardt "An Algorithm for Least-Squares Estimation of Nonlinear Parameters" Isoc. Indust. Appl. Math. (SIAM), Vol. II, No. 2, pp. 431–441; and Yonathan Bard, "Nonlinear Parametric Estimation," Academic Press, New York, N.Y., 1974. These references are incorporated herein by reference in their entireties and for all purposes. The Marquardt-Levenberg method stabilizes overdetermined systems during minimization of the cost function. The relevant matrix equation for minimizing the sum of squares of residuals may be represented as follows:

$$\begin{bmatrix} \frac{\partial f_i}{\partial \delta_i}, \ldots 0, \frac{\partial f_i}{\partial \delta_m}, \ldots \frac{\partial f_i}{\partial \beta_i}, \ldots \frac{\partial f_i}{\partial \beta_l}, \ldots \\ \vdots \\ \frac{\partial f_i}{\partial \delta_i}, \ldots \frac{\partial f_i}{\partial \delta_l}, 0, \ldots \frac{\partial f_i}{\partial \beta_i}, \ldots 0, \frac{\partial f_i}{\partial \beta_m}, \ldots \\ \vdots \end{bmatrix} \begin{bmatrix} \Delta \delta_i \\ \vdots \\ \Delta \delta_n \\ \Delta \beta_i \\ \vdots \\ \Delta \beta_p \end{bmatrix} = \begin{bmatrix} r_i \\ \vdots \\ r_i \\ \vdots \end{bmatrix}$$

Here the matrix on the left hand side of the equation is the gradient matrix (sometimes referred to as a Jacobian) of the response curve functions. Each row corresponds to a different data point j, and each column corresponds to a different unknown structural parameter, β, or correction value, δ, to the sample value. The individual elements of the gradient matrix are the first derivatives of the response curve functions with respect to either a structural parameter or a correction value. For example, the element in the first column of the first row (j=1) might be the derivative of the response curve expression (e.g., a quadratic expression) for the method used to analyze the first data point with respect to the curvature, k, for that expression. The derivative is evaluated for the current values of the parameters and correction factors appearing therein; that is, the parameters and correction factors of the current iteration. The element in the second column in the first row of the gradient matrix will be the derivative of the same response curve expression but with respect to a different parameter or correction value—possibly the correction factor δ1. The remainder of the first row is populated with derivatives of the expression at the first data point with respect to each unknown parameter and correction value in the entire system. The second row is similarly populated, but this time with derivatives of the function at the second data point; i.e., the response curve of the method used to analyze the second data point and evaluated at the second data point. There is one row for each data point in the gradient matrix. And there is a column for each unknown parameter and correction value.

The residual vector, $R_j$, on the right hand side of the matrix equation is just the value of the residual, R, for each data row. Thus, there is a row for each data point in the data set. The residual values are calculated per the above equation for R.

It should be understood that each and every data point may be represented as a row in the gradient matrix (and an entry in the residual matrix). This includes replicate measurements taken for a single sample/assay combination. As mentioned, there will be some spread or intrinsic noise (typically a Gaussian) in the measured values taken for each sample/assay combination. The technique described herein handles such noise considering each of the replicate measurements taken and provides the best curve fit through them on the best representation of x-axis spacing between samples.

As shown, the gradient matrix is multiplied by a vector delta values. These are the changes—between iterations—for each unknown structural parameter and correction value. The number of rows in this vector equals the total number of unknown structural parameters and correction values. Thus, the number of rows in the delta vector equals the number of columns in the gradient matrix. The delta vector is the unknown quantity which is solved for in each iteration. The delta values of the parameters are added to the values of those parameters from the previous iteration to obtain the improved values of the parameters for the next iteration.

To solve this matrix equation for the delta parameter values, a modified "least squares projector" may be employed. Using this technique, the delta vector is solved according to the following equation:

$$\begin{bmatrix} \Delta \vec{\delta} \\ \Delta \vec{\beta} \end{bmatrix} = \left\{ \begin{bmatrix} \nabla f \\ (\vec{\delta}, \vec{\beta}) \end{bmatrix}^T \begin{bmatrix} \nabla f \\ (\vec{\delta}, \vec{\beta}) \end{bmatrix} + \lambda \right\}^{-1} \begin{bmatrix} \nabla f \\ (\vec{\delta}, \vec{\beta}) \end{bmatrix}^T [R]$$

In a normal least squares projector, the gradient matrix is multiplied by its transpose and the inverse of resulting square matrix is taken. This inverse is then multiplied by the transpose of the gradient matrix and that result is multiplied by the residual vector. This approach will give the delta vector, but it may be unstable due to singularities (i.e., the system may divide by zero during the operation of the least squares projector without some modification).

To address this instability, the Marquardt-Levenberg approach introduces a scalar factor, λ>0, as indicated in the above expression. Specifically, λ is added to the product of the gradient matrix and its transpose before the resulting square matrix is inverted. By adding the scalar λ, the system avoids singularities. An intial value, $\lambda_0$, is guessed and then adjusted (typically by trial and error) until the value of the objective function is reduced. Generally, the value of $\lambda_0$ is chosen to be as small as possible (about 0.01 in one specific example). The smaller the value of λ, the faster the overall problem converges to a solution. However, for each iteration, the value of λ must be sufficiently large that the system is stable and that the sum of the squares of the residuals is actually reduced in comparison to the previous iteration.

With the delta values now in hand, the parameters and correction factors for the next iteration (iteration i+1) are calculated as follows:

$$\delta_{i+1} = \delta_i + \Delta \delta_i$$

$$\beta_{i+1} = \beta_i + \Delta \beta_i$$

At this point, the objective function (sum of squared residuals in this example) is evaluated.

This may be accomplished by putting the values of $\delta_{i+1}$ and $\beta_{i+1}$ back into the expressions for the residual vector and then multiplying that newly evaluated residual vector by its transpose. Then the computer system determines whether the current value of the objective function is less than the previous value of that function. If the objective function is in fact less than in the previous iteration, the value of λ is made smaller. The new value of the objective function is calculated. If it is still smaller, then λ is again reduced. This continues until the value the objective function increases over that of the previous iteration. All this takes place for a given iteration. If the initial value of λ generates a objective function that is greater than that of the previous iteration, then the value of λ is increased until the objective function falls below that of the previous iteration.

After each such iteration, the new parameter values are put in the above matrix equation to generate new delta vectors until some criterion for stopping is reached. Generally, suitable criteria require that the delta vector or the objective function becomes quite small. For example, the iterations may cease when the one of these reaches zero. Sometimes, the correction vector or objective function will not quickly reach zero. To account for such cases, a stopping criterion may be a suitably small value of these over multiple iterations.

When the stopping criterion is reached, all structural parameters for the response curves are known as are the correction factors to the true property values of the samples. The computer system then outputs these solved values. The outputs are then provided as expressions for the response curves of each method as a function of a common independent variable (the true property values of the samples). These expressions may be plotted together to allow visual comparison of their responsiveness, sensitivity, linearity, etc.

In one example, the resulting nomogram may be used to convert values of one assay to the equivalent value obtained by another assay according to the following four steps procedure.

1. Locate the assay value to be converted on the left side scale of the plot (the y-axis).
2. Move right, parallel to the x-axis until that assay's curve is located.
3. Next, move up or down parallel to the y-axis until the curve of the assay whose comparative value is desired.

4. Finally, move parallel to the x-axis back to the assay scale to read the expected value of the comparative assay.

While the above discussion has presented a two dimensional problem (measured y-values versus underlying or true property x-values), there is in principle no reason why the computer techniques of this invention can not be applied to systems having additional dimensions (axes).

Those additional dimensions or axes represent other independent variables (x values) manifesting the same underlying condition or state of the physical system. For example, the disease hepatitis B represents an underlying condition having multiple manifestations, each of which provides a separate independent variable (x-axis). These manifestations may be (1) concentration of HBV DNA, (2) concentration of HBV surface antigen (HBSAg), (3) concentration of immunoglobulins to HBV, etc. Various assays measure these various manifestations of hepatitis B disease. If clinical samples from heptitis B patients are tested with these various assays, the results may be normalized with a method of the type described above. For example, a sum of least squares objective function may be minimized by an iterative technique such as the above-described Marquardt-Levenburg technique. However, the data will be provided for two more independent variables. Thus, correction factors for the samples to be corrected are provided for each of the independent variable axes. Such techniques allow normalization of data across multiple independent axes to permit greater insight into the underlying phenomenon (e.g., hepatitis B disease).

D. APPLICATIONS

Various applications for the techniques of this invention are possible. One important application is conversion among results from different assays. This allows physicians or others working with multiple measurement techniques to use data from all techniques with confidence that the data can be interpreted consistently. For example, an HIV patient may periodically receive a blood analysis in which HIV viral load is monitored by a first method. However, one reading is made by a second method (which quantitates by a fundamentally different mechanism than the first method). Using the conversions afforded by this invention, a physician interpreting the data from both methods can be confident that his reading of the second assay results provide an HIV viral load that is consistent with the readings from the first assay.

The multi-measurement technique also allows construction of models that draw on data from two more different assays. Before this invention, when no reliable method for converting between results of multiple assays was available, one was limited to models that employed data from a single assay. Now the combined results from multiple assays can generate the model, validate the model, and/or provide inputs to execute the model.

The multi-measurement technique of this invention can also compare the performance of the multiple methods that it compares. Prior to this invention, it was impossible to compare three or more distinct measurement methods by a single regression analysis. Traditional regression analysis is also unable to distinguish the error rate or the intrinsic bias of the evaluated assays.

Aspects of assay performance are contained within the equation of quadratic assay curves which are written in the form: $y=kx^2+mx+b$. The curvature (k) provides an indication of the linearity of the assay; the lower the curvature (k approaches 0), the more linear the assay. The slope (m) is an average measure of the responsiveness of the assay throughout its dynamic range, in other words, how measured analyte quantification values change in response to the approximated "true" analyte concentration (i.e, the sensitivity at x). The slope at any particular point along the curve (the instantaneous slope) may be derived from the equation: $dy/dx=2kx+m$. The greater the instantaneous slope, the greater the responsiveness of the assay at any given point within the dynamic range of the assay. Finally, the precision of each assay is indicated by the amount of scatter which is represented by the $R^2$ value, a measure of how closely the assay curve fits the data set. A higher number indicates less scatter and therefore a greater degree of precision. Optionally, the standard deviation (estimated noise spread about the curve) is a suitable measure of precision for each assay.

Another application for the multi-measurement technique is to assess and develop standards for new assays. Standards give assays a common reference so that relative comparisons have meaning. Typically, an assay is calibrated against a standard which supposedly represents some fixed value of the independent variable (e.g., analyte concentration). This presents two problems. First, some standards, particularly those used for biological assays, can degrade or "float" with time. In such cases, the standard moves over time. Second, when a standard is used up, an enterprise must produce a new batch of standard. Unfortunately, it can be very difficult to produce fresh standards which accurately reproduce the preceding standard(s). It is not uncommon for assigned (but unknown) property values for bioassay standards to be off by 20 to 30 percent. Thus, the new standard must always be calibrated against the old. This involves the same conversion problems discussed above with respect to multiple assays.

Since it leverages the relative spacing of x-values of samples, the multiple measurement techniques of this invention can be used to assist in generating new standards and comparing existing standards. First, biochemists (or other technical personnel) making the new batches of standards can check the putative standards against previous standards using the multi-measurement technique to determine whether the new standard is sufficiently close to the old. If not, the new standard can be adjusted or reformulated until it reaches a level sufficiently close to the old standard. Second, the multi-measurement technique can exactly quantify any separation between the new and old standards. This information is then used to modify the calibration curves or software provided with assays employing the new standard. Still further, the multi-measurement technique can check the quality of assays going out the door (i.e., quality control).

Like any other application of the inventive technique, more than one measurement method must be used to analyze the standard. Obviously, distinct methods could be used. Often, however, it would be more convenient to use a single method (e.g., one company's assay for HBV). In such cases, different "versions" of the same assay can be used. Note the definition of "different" methods can be quite general, e.g. the same assay under "different" circumstances such as different plates, different calibrator batches, or different types of calibrator. Since the methods are measuring the same samples, inherent in their measurements should be the essence of a common target (communality) but from different "angles." In effect, no one method produces the correct answer, but assuming reasonable distribution about the true value, the ensemble result from all methods is expected to be more accurate. Hence, a self-consistent approach provides excellent information on this common but unknown target (the new standard). Each method produces a "y" value (typically logarithm of the method reading), representative of the analyte level in the standard. Since an assay "A" is judged worldwide by other assays, using those other assays with assay "A," to leverage quantiation standards for assay "A" assures the best possible worldwide rating for assay "A."

E. EXAMPLES

Specimens (247) from patients with chronic hepatitis B were evaluated for Hepatitis B virus (HBV) DNA using three commercial assays—Chiron Quantiplex™ (CA), Digene Hybrid Capture (DA) and Abbott HBV DNA assay (AA). The results were used to generate a multi-measurement technique nomogram that compared the assay's linearity, responsiveness and precision, and allowed conversion between the different assay values. The multi-measurement technique analysis showed the CA to be more sensitive and responsive than the DA and AA. Both CA and DA were more precise than AA. Cross validation of the multi-measurement technique results was performed using two additional data sets of 500 and 200 paired specimens, respectively.

Clinical Specimens

A total of 247 serum specimens were obtained from 76 chronic hepatitis B patients. 113 of these specimens were sequential specimens obtained from patients receiving interferon therapy as part of a interferon re-treatment trial. All specimens were originally tested for HBV DNA by the CA. Subsequently, subsets of specimens were tested by the DA and AA. In all, 113 were independently assayed by all three HBV DNA quantification assays, 114 by the CA and AA only, and 20 by the CA and DA only. All sera were separated within four hours of collection and either immediately frozen at −70° C. or kept at 4° C. for 24–28 hours prior to freezing at −70° C. Sera underwent only one freeze-thaw cycle prior to HBV DNA testing.

HBV DNA Quantification

All three assays were performed according to the instructions of their manufacturers. CA (Chiron Corporation, Emeryville, Calif.) uses a series of synthetic oligonucleotide probes to bind single-stranded HBV DNA molecules to a solid phase and uses branched DNA (bDNA) technology to generate a chemiluminescent signal which corresponds to the amount of HBV DNA target in the specimen. For the CA, all specimens were tested in duplicate, and the concentration of HBV DNA in each specimen was determined from a standard curve. DA (Digene Diagnostics, Inc., Beltsville, Md.) uses HBV-RNA probes to capture single stranded HBV DNA molecules to a solid phase, and anti-RNA:DNA hybrid antibodies conjugated to alkaline phosphates to generate a chemiluminescent signal. For the DA, specimens were tested individually and the concentration of HBV DNA in each specimen was determined by comparison to the chemiluminescent signals derived from controls which were tested in duplicate. AA (Abbott Laboratories, Abbott Park, Ill.) is a liquid hybridization assay in which HBV DNA is hybridized to single-stranded $^{125}$I-HBV DNA probes and unhybridized DNA is removed by sepharose chromatography. For the AA, specimens were tested individually and the concentration of HBV DNA in each specimen was determined by comparison to the radioactivity of positive and negative controls.

Comparison of Assay Performance

Of the three assays, the CA exhibited better performance with regards to linearity, responsiveness and precision. The k value (curvature), a measure of assay linearity, for the cA was lower than the k values for the DA or AA (0.15 versus 0.61 and 0.81, respectively). Both CA and DA had less scatter, as indicated by higher $R^2$ values, than the AA (0.9951 and 0.9946 versus 0.9614, respectively).

Conversion between Assay Values

Figure 5:
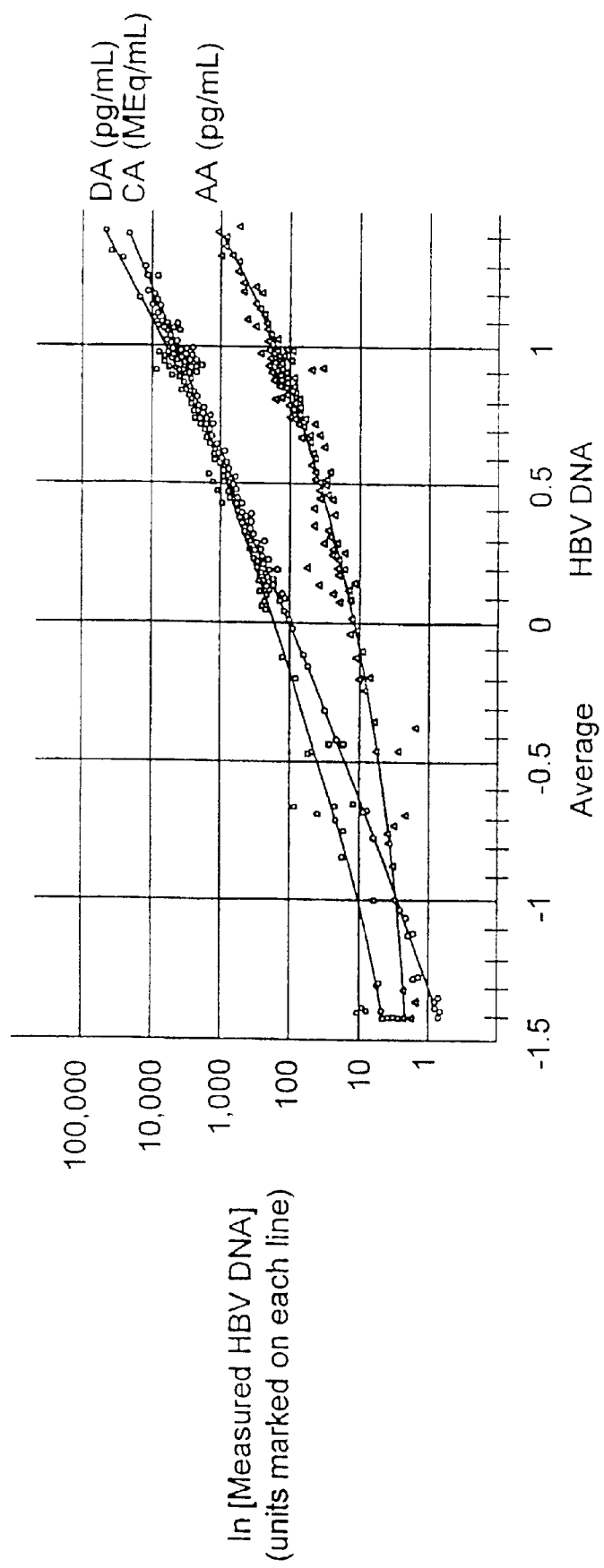
FIG. 5 is a nomogram showing response curves for three different HBV-DNA assays as generated by the techniques of this invention. The response curves were fit to quadratic expressions.

The multi-measurement technique nomogram also provides a means to convert between the different assay values. Conversion of assay values may be accomplished by using the assay curves shown in FIG. 5 to compare "y" values between assays for a given "x" value, or by using the equations shown in FIG. 6. Examples showing the conversion of a CA value of 100 Meq/ml to a DA value of 150 pg/ml using both the assay curves and the equations are described below.

Using the assay curves to convert a CA value of 100 Meq/ml to a DA value in pg/ml one would: 1) locate 100 on the y-axis, 2) move horizontally away from the y-axis to the CA curve, 3) move vertically up to the DA curve, and 4) move horizontally toward the y-axis to read 150.

Using the equations to convert a CA value of 100 Meq/ml to a DA value in pg/ml one would: 1) set y equal to 100 and solve the equation "$y=0.15x^2+3.79x+4.96$ to obtain a value for x, and 2) use this x-value to solve the equation "$y=0.61x^2+3.34x+5.21$" and obtain a value of 150 for y.

It is important to recognize that, although there is overlap between the dynamic range of the different assays, specimens whose values fall beyond the dynamic range of a given assay (e.g. DA values >2000 pg/ml) must be diluted in HBV DNA negative serum and be re-tested to obtain an accurate viral load measurement. Similarly, the AA is unable to accurately quantify specimens containing <4–5 pg/ml.

Cross Validation of Multi-Measurement Method

The ability of the multi-measurement technique to accurately convert between assay values was tested in two ways: (1) by comparing the multi-measurement technique-derived relationships with previously published relationships, and (2) by comparing the multi-measurement technique-derived quantification values with measured values from an independent data set. For the first analysis, the multi-measurement technique-derived relationship between the CA and AA was compared to a previously-published relationship between the CA and AA that was derived using linear regression techniques (Kapke, G. F., G. Watson, S. Sheffler, D. Hunt, and C. Frederick. 1997 "Comparison of the Chiron Quantiplex branched DNA (bDNA) assay and the Abbott Genostics solution hybridization assay for quantification of hepatitis B viral DNA" J Viral Hepatitis. 4:67–75). The correlation coefficient between the multi-measurement technique and linear regression curves was 0.995 for HBV DNA quantification values above 100 Meq. The close correlation between these CA and AA relationships is likely because the more precise CA values were plotted on the x-axis for the linear regression analysis, thereby providing a greater degree of agreement between the linear regression and multi-measurement technique curves.

The ability of the multi-measurement technique to accurately convert between DA and CA values was assessed by testing a separate cohort of 100 chronic hepatitis B patients by both assays. The measured DA values then were compared with the values predicated by the multi-measurement technique based on the CA values. There was a close correlation between the measured DA values (observed HBV DNA) and the multi-measurement technique-predicated DA values (expected HBV DNA). The correlation coefficient ($R^2$) for this analysis was 0.96.

The multi-measurement technique-derived correlations are consistent with previous observations. The greater linearity of the CA as compared to the DA and AA has been noted in a recent study by Butterworth and colleagues (Butterworth, L. -A., S. L. Prior, P. J. Buda, J. L. Faoagali, and G. Cooksley. 1996 "Comparison of four methods for quantitative measurement of hepatitis B viral DNA" J Hepatol. 24:686–691). With regard to precision, the CA consistently has been reported to exhibit the best performance, although the relative performance of the DA and AA varies (Butterworth, L. -A., S. L. Prior, P. J. Buda, J. L. Faoagali, and G. Cooksley 1996 "Comparison of four methods for quantitative measurement of hepatitis B viral DNA" J Hepatol. 24:686–691; Kapke, G. F., G. Watson, S. Sheffler, D. Hunt, and C. Frederick. 1997 "Comparison of the Chiron Quantiplex branched DNA (bDNA) assay and the Abbott Genostics solution hybridization assay for quantification of hepatitis B viral DNA" J Viral Hepatitis 4:67–75). The greater sensitivity (i.e. greater responsiveness at the lower end of the dynamic range) of the CA over the DA and/or AA also has been noted in several studies (Zaaijer, H. L., F. ter Borg, H. T. M. Cuypers, M. C. A. H. Hermus, and P. N. Lelie. 1994 "Comparison of methods for detection of hepatitis B virus DNA" J Clin Microbiol. 32:2088–2091; Butterworth, L.- A., S. L. Prior, P. J. Buda, J. L. Faoagali, and G. Cooksley. 1996 "Comparison of four methods for quantitative measurement of hepatitis B viral DNA" J Hepatol. 24:686–691; Kapke, G. F., G. Watson, S. Sheffler, D. Hunt, and C. Frederick. 1997 "Comparison of the Chiron Quantiplex branched DNA (bDNA) assay and the Abbott Genostics solution hybridization assay for quantification of hepatitis B viral DNA" J Viral Hepatitis. 4:67–75; Pawlotsky, J. M., A. Bastic, I. Lonjon, J. Remire, F. Darthuy, C. J. Soussy, and D. Dhumeaux 1997 "What technique should be used for routine detection and quantification of HBV DNA in clinical samples?" J Virol Methods. 65:245–253).

Limited Overlap Example

The multiple measurement technique of this invention was used to assess the performance characteristics of the Roche AMPLICOR HBV Monitor PCR Test (RA) and its relationship to the Chiron Quantiplex® HBV DNA assay (CA), Digene Hybrid Capture™ (DA), and Abbott HBV DNA assays (AA). We tested in duplicate sixty specimens previously evaluated by the above-described HBV DNA assays by the RA and generated a new multi-measurement technique graph incorporating the results from all 4 assays. The curves generated by the multi-measurement technique method demonstrate excellent concordance between the CA and the RA in the small area of overlap ($R^2$=0.99). They also define the region of overlap of the RA and CA to be 0.7–8 MegaEquivalents/mL (MEq/mL)=700,000–8,000,000 copies/mL (or 2.5–28.2 pg/ml) based on the high end plateau of the RA. A preliminary sensitivity analysis using clinical specimens conservatively approximates the minimum detection limit of the RA—defined as the value above which specimens can be considered positive with 95% certainty (approx. 3500 copies/ml). In addition, the reliable detection limit of the RA—the value at which one can reliably quantify specimens with 95% confidence—appears to be higher. Based on our data, the RA appears approximately 3 logs more sensitive than the CA and DA. Of 512 specimens tested for HBV DNA, 268/512 (52%) quantify as <0.7 MEq/mL, 52/512 (10%) quantify between >0.7 and <8 MEq/mL and 192/512 (38%) quantify as >8 MEq/mL. Thus given the upper limit of quantification of the RA which is estimated to be approx. 8 MEq/mL, 38% of next specimens tested for HBV DNA will be beyond the dynamic range of the RA.

Figure 7A:
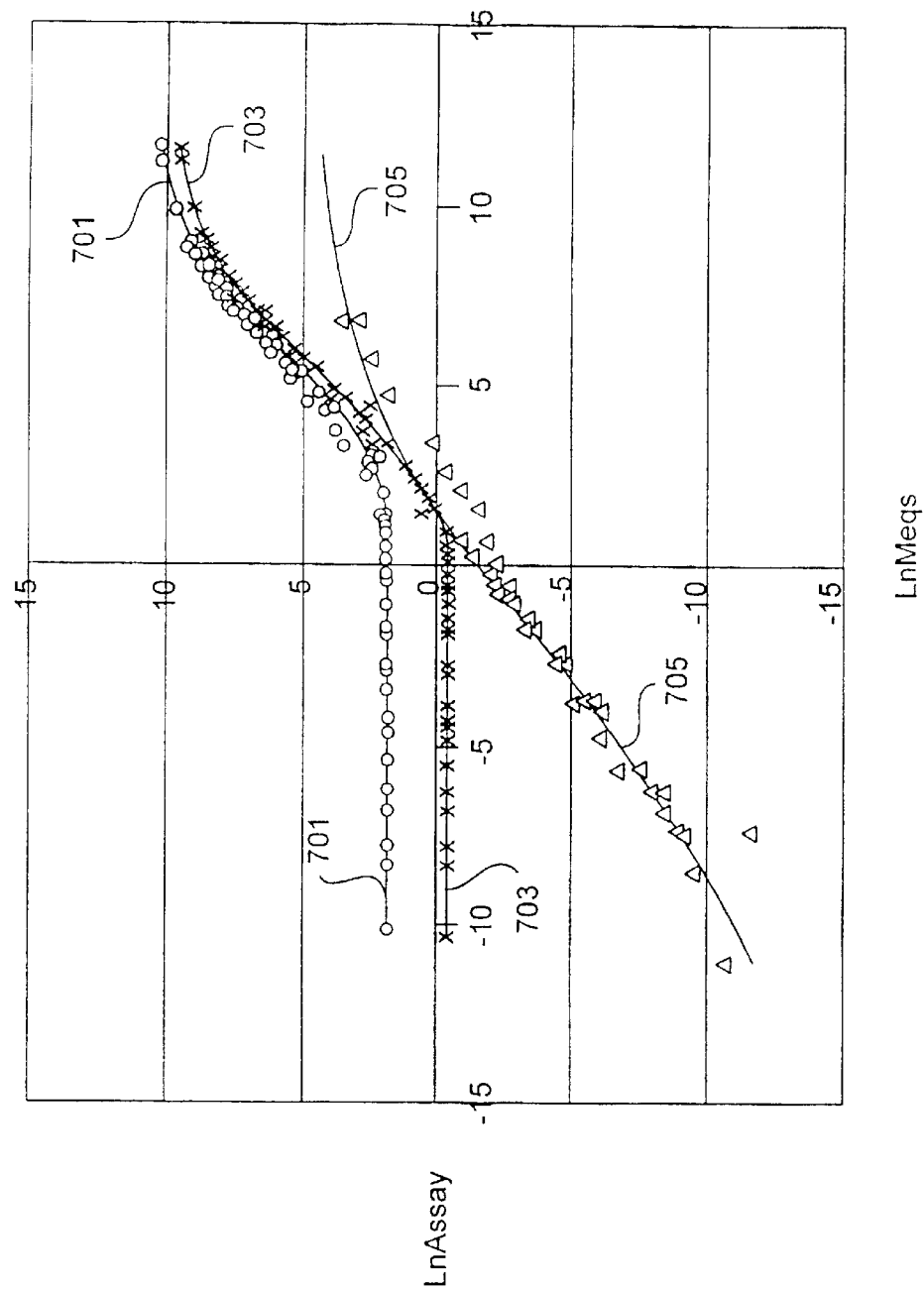
FIG. 7A is nomogram showing response curves for three different HBV-DNA assays as generated by the techniques of this invention. The response curves were fit to sigmoidal expressions.

To facilitate comparison of assay performance and coversion between assay values for those assays that share a common dynamic range, a nomogram was generated with contains response curves for the CA, DA, and RA assays. See FIG. 7A. The DA results (circles) are fit to a curve 701, the CA results (Xs) are fit to a curve 703, and the RA results (triangles) are fit to a curve 705. The assay results were plotted on a logarithm transformed scale, where the y-axis indicates measured HBV DNA levels in the specimens measured by each of the three assays (in the various assay units), and the x-axis indicates the approximated "true" HBV DNA in each specimen as generated by the technique of this invention.

Figure 7B:
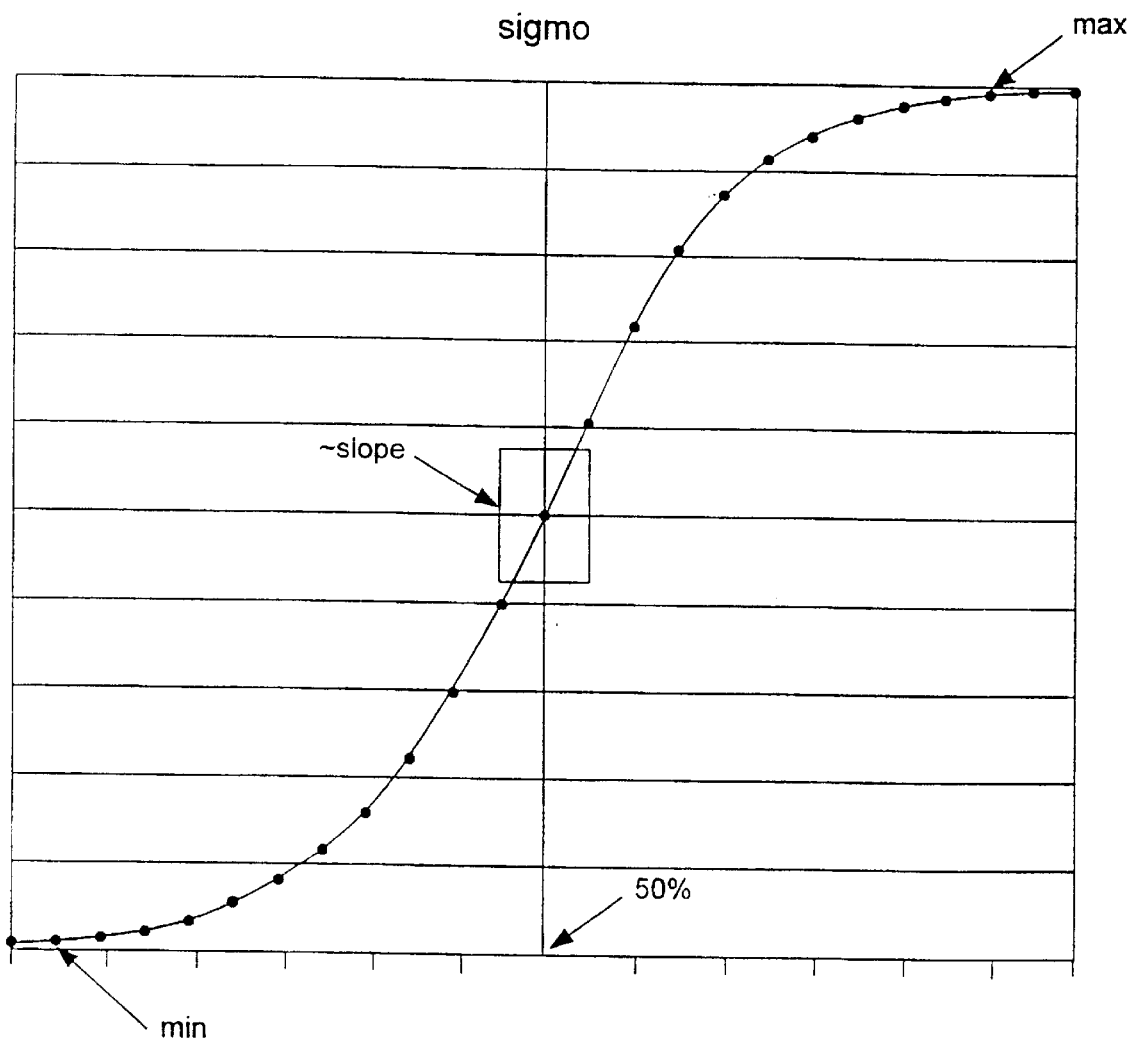
FIG. 7B is a plot illustrating the features of a sigmoidal response curve as used to generate the nomogram presented in FIG. 7A.

In this analysis, each assay's response curve was indicated by a four parameter sigmoid curve: minimum, maximum minus minimum, slope, and the 50 percent point. These parameters are illustrated in FIG. 7B.

H. ADDITIONAL EMBODIMENTS

While this invention has been described in terms of several preferred embodiments, it is contemplated that alternatives, modifications, permutations and equivalents thereof will become apparent to those skilled in the art upon a reading of the specification and study of the drawings. It is therefore intended that the following appended claims include all such alternatives, modifications, permutations and equivalents as fall within the true spirit and scope of the present invention.

What is claimed is:

1. A computer implemented method of normalizing at least two measurement methods, the method comprising:
   receiving data specifying measured values versus physical properties for samples evaluated by the measurement methods, wherein the data includes (i) at least two first sample data points which were obtained from a first sample analyzed with at least two of the measurement methods and (ii) at least two second sample data points which were obtained from a second sample analyzed with at least two of the measurement methods;
   assuming a value for the physical property of the first sample and assuming a value for the physical property of the second sample;
   for each of the measurement methods, assuming a mathematical form of a response curve describing the measured values as a function of the physical properties, wherein the forms of expression contain unknown parameter values; and
   simultaneously solving for all the unknown parameter values and a correction factor for the value of the physical property of the second sample.

2. The method of claim 1, further comprising providing a nomogram including solved response curves or solved mathematical expressions for at least two of the measurement methods.

3. The method of claim 1, wherein the data received includes at least enough data points to fully determine the parameters values of the response curve, the correction factor for the second sample, and any additional correction factors.

4. The method of claim 1, wherein the measurement methods are assays.

5. The method of claim 1, wherein the measurement methods are assays for biological materials.

6. The method of claim 1, wherein the measured values include at least one of luminescence, radioactivity, and color intensity.

7. The method of claim 1, further comprising setting the value for the physical property of the first sample as an anchor value, wherein during simultaneously solving for all the unknown parameter values the anchor value is not provided with a correction value.

8. The method of claim 1, wherein the mathematical forms of the response curves include at least one of linear expressions, quadratic expressions, and sigmoidal expressions.

9. The method of claim 1, wherein the method simultaneously solves for one or more additional correction factors associated with physical quantities of additional samples for which data was received.

10. A computer program product for normalizing response curves of plurality of measurement methods, the computer program product comprising:
   (a) a computer readable medium; and
   (b) instructions, stored on the computer readable medium, for normalizing the response curves, the instructions comprising
      (i) receiving data specifying measured values versus physical properties for samples evaluated by the measurement methods, wherein the data includes (i) at least two first sample data points which were obtained from a first sample analyzed with at least two of the measurement methods and (ii) at least two second sample data points which were obtained from a second sample analyzed with at least two of the measurement methods;
      (ii) assuming a value for the physical property of the first sample and assuming a value for the physical property of the second sample;
      (iii) for each of the measurement methods, assuming a mathematical form of a response curve describing the measured values as a function of the physical properties, wherein the forms of expression contain unknown parameter values; and
      (iv) simultaneously solving for all the unknown parameter values and a correction factor for the value of the physical property of the second sample.

11. The computer program product of claim 10, where the instructions further comprise providing a nomogram including solved response curves or solved mathematical expressions for at least two of the measurement methods.

12. The computer program product of claim 10, wherein the data received includes at least enough data points to fully determine the parameters values of the response curve, the correction factor for the second sample, and any additional correction factors.

13. The computer program product of claim 10, wherein the measurement methods are assays.

14. The computer program product of claim 10, wherein the measurement methods are assays for biological materials.

15. The computer program product of claim 10, wherein the measured values include at least one of luminescence, radioactivity, and color intensity.

16. The computer program product of claim 10, wherein the instructions further comprise setting the value for the physical property of the first sample as an anchor value, wherein during simultaneously solving for all the unknown parameter values the anchor value is not provided with a correction value.

17. The computer program product of claim 10, wherein the mathematical forms of the response curves include at least one of linear expressions, quadratic expressions, and sigmoidal expressions.

18. The computer program product of claim 10, wherein the instruction (iv) simultaneously solves for one or more additional correction factors associated with physical quantities of additional samples for which data was received.

19. A computer implemented method of normalizing at least two measurement methods, the method comprising:
   receiving data specifying measured values versus physical properties for samples evaluated by the measurement methods;
   using the data to simultaneously solve for
   (i) structural parameters defining the shape of response curves for each assay, and
   (ii) one or more correction factors adjusting the relative positions of physical property values assumed for the samples; and
   outputting expressions for the response curves of each assay normalized on a common axis representing the physical property values.

20. The method of claim 19, wherein simultaneously solving for structural parameters and correction factors involves mininimizing an objective function.

21. The method of claim 20, wherein simultaneously solving for structural parameters and correction factors employs a regression technique which minimizes the sum of the squares of the residuals of the data points.

22. The method of claim 20, wherein simultaneously solving for structural parameters and correction factors employs a Marquardt-Levenberg technique.

23. The method of claim 19, wherein the received data includes replicate measurement values of a given sample by a given assay.

24. The method of claim 19, wherein simultaneously solving for structural parameters and correction factors involves generating response curve expressions for each received data point and iteratively correcting the values of structural parameters and correction factors until convergence.

25. The method of claim 19, further comprising creating a nomogram from the output normalized expressions for the response curves.

* * * * *